United States Patent [19]

Kleiner et al.

[11] 3,939,050
[45] Feb. 17, 1976

[54] PROCESS FOR THE PREPARATION OF ETHANE-1,2-DIPHOSPHINIC ACID DIESTERS

[75] Inventors: Hans-Jerg Kleiner, Bad Soden, Taunus; Sigurd Rösinger, Frankfurt am Main, both of Germany

[73] Assignee: Hoechst Aktiengesellschaft, Frankfurt am Main, Germany

[22] Filed: Jan. 17, 1974

[21] Appl. No.: 434,029

[30] Foreign Application Priority Data
Mar. 19, 1973 Germany............................ 2313581

[52] U.S. Cl......................................... 204/162 HE
[51] Int. Cl.²........................................... B01J 1/10
[58] Field of Search ............... 204/162 HE; 260/970

[56] References Cited
UNITED STATES PATENTS
3,673,285  6/1972  Lin......................... 260/970
3,681,219  8/1972  Oswald.................. 204/162 HE

*Primary Examiner*—Leland A. Sebastian
*Attorney, Agent, or Firm*—Curtis, Morris & Safford

[57] ABSTRACT

A process for the preparation of ethane-1,2-diphosphinic acid diesters of the formula

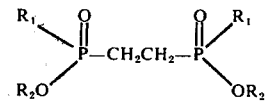

where $R_1$ represents alkyl, phenyl and/or phenalkyl groups having from 1 to 18 carbon atoms and $R_2$ alkyl groups having from 1 to 18 carbon atoms, which may be optionally substituted by halogen atoms, which comprises reacting phosphonous acid esters of the formula

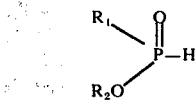

where $R_1$ and $R_2$ are as defined above, with acetylene using high-energy irradiation.

7 Claims, No Drawings

PROCESS FOR THE PREPARATION OF ETHANE-1,2-DIPHOSPHINIC ACID DIESTERS

Copending Application Ser. No. 434,030 filed concurrently herewith on Jan. 17, 1974 describes a process for the preparation of ethane-1,2-diphosphinic acid diesters of the formula

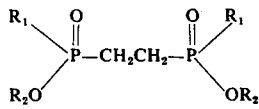

where $R_1$ represents alkyl, phenyl and/or phenalkyl groups having from 1 to 18 carbon atoms and $R_2$ alkyl groups having from 1 to 18 carbon atoms, which may be optionally substituted by halogen atoms, which comprises reacting phosphonous acid esters of the formula

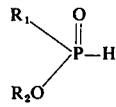

where $R_1$ and $R_2$ are as defined above, with acetylene in the presence of catalytic amounts of radical-forming agents and/or with UV irradiation.

It has now been found that the reaction of phosphonous acid esters with acetylene may also be activated by the influence of high-energy irradiation, preferably by gamma or X-rays. Also accelerated electrons having an energy of from about 0.5 to 4 megavolts or the irradiation of a nuclear reactor may be used. The dosage of the irradiation may widely vary from $3 \cdot 10^{-3}$ W/kg ($10^3$ rd/h) to $3 \cdot 10^3$ W/kg ($10^9$ rd/h). In the case where for example the gamma-rays of a cobalt-60 source are employed, the dose rate is generally from $3.10^{-3}$ W/kg ($10^3$ rd/h) to 30 W/kg ($10^7$ rd/h).

The total irradiation dose, depending on the conversion rate desired and the dose rate used, is from 10 J/kg ($10^3$ rd) to $10^5$ J/kg (10 Mrd), preferably from $10^3$ J/kg (0.1 Mrd) to $10^5$ J/kg (10 Mrd). The reaction may be carried out in a temperature range of from 80° to 180°C, preferably from 80° to 140°C. Higher temperatures may be employed, but they are not advantageous.

As material for the reaction zone, any material inert under the reaction conditions may be used, for example glass, furthermore steel, nickel or the alloys thereof.

It is a special advantage of the process of the present invention that the use of radical-forming agents is no longer required, which ensures a decrease of manufacturing cost and the obtention of final products having a higher degree of purity. According to the process of our copending application, the reaction may be carried out also with UV irradiation; the use of radical-forming agents being nevertheless necessary, which requires temperatures of from 140° to 230°C, preferably from 170°–200°C. According to the process of the present invention, however, it is possible to operate at lower temperatures, which suppress side-reactions, so that the process is simplified and a purer final product is obtained.

The following examples illustrate the invention.

EXAMPLE 1

In a cylindrical vessel which may be heated or cooled and which is provided with a gas feeder frit, 500 g of a mixture of 75 weight % of methane-phosphonous acid isobutyl ester and 25 weight % of isobutanol are maintained at 130°C by means of a thermostat. After flushing with pure nitrogen, acetylene is introduced into the mixture with vigorous agitation, while the mixture is exposed to a cobalt-60-gamma irradiation at a dose rate of 0.44 W/kg ($1.6 \cdot 10^5$ rd/h). The acetylene is fed in to that extent to which it is absorbed. During the reaction, the reaction temperature rises temporarily to 143°C because of the reaction heat. After 6 hours and a total dose of $9.6 \cdot 10^3$ J/kg (0.96 Mrd), the reaction is substantially complete. By distillation of the reaction mixture, 345 g of ethane-1,2-dimethyl-phosphinic acid diisobutyl ester are obtained, which corresponds to a yield of 84 %.

EXAMPLE 2

In the apparatus described in Example 1, 195 g of a mixture of 75 weight % of methane-phosphonous acid-isobutyl ester and 25 weight % of isobutanol are heated to 125°C. Acetylene is introduced into the mixture with vigorous agitation, while the mixture is exposed to a cobalt-60-gamma irradiation at a dose rate of 0.9 W/kg ($3.2 \cdot 10^5$ rd/h). The acetylene is fed in to that extent to which it is absorbed. Because of the exothermal reaction, the reaction temperature rises temporarily to 134°C during the reaction period. After 2½ hours, and a total dose of $8 \cdot 10^3$ J/kg (0.8 Mrd), the reaction is substantially complete. By distillation, 130 g of ethane-1,2-dimethylphosphinic acid di-isobutyl ester are obtained, which corresponds to a yield of 81 %.

We claim:

1. In a process for the preparation of an ethane-1,2-diphosphinic acid diester of the formula

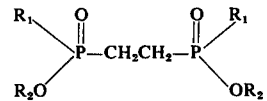

wherein $R_1$ represents an alkyl, phenyl or phenalkyl group having from 1 to 18 carbon atoms and $R_2$ is an alkyl group or a halogen substituted alkyl group having from 1 to 18 carbon atoms by reacting with acetylene a phosphorous acid ester of the formula

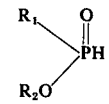

wherein $R_1$ and $R_2$ are as defined above, the improvement which comprises activating the reaction with high-energy irradiation.

2. A process as claimed in claim 1, wherein gamma-rays are used for high-energy irradiation.

3. A process as claimed in claim 1, wherein X-rays are used for high-energy irradiation.

4. A process as claimed in claim 1, wherein accelerated electrons are used for high-energy irradiation.

5. A process as claimed in claim 1, wherein the nuclear rays of a nuclear reactor are used for high-energy irradiation.

6. A process as claimed in claim 1, wherein the reaction is carried out at dose rates of from $3 \cdot 10^{-3}$ W/kg ($10^3$ rd/h) to $3 \cdot 10^3$ W/kg ($10^9$ rd/h), preferably from $3 \cdot 10^{-3}$ R/kg ($10^3$ rd/h) to 30 W/kg ($10^7$ rd/h).

7. A process as claimed in claim 1, wherein for the reaction total doses of from $10^3$ J/kg (0.1 Mrd) to $10^5$ J/kg (10 Mrd) are used.

* * * * *